United States Patent
Bucur et al.

(10) Patent No.: US 10,629,295 B2
(45) Date of Patent: Apr. 21, 2020

(54) SUPPORTING EXECUTION OF A CLINICAL TRIAL

(71) Applicant: KONINKLIJKE PHILIPS N.V., Eindhoven (NL)

(72) Inventors: Anca Ioana Daniela Bucur, Eindhoven (NL); Richard Vdovjak, Eindhoven (NL)

(73) Assignee: KONINLIJKE PHILIPS N.V., Eindhoven (NL)

( * ) Notice: Subject to any disclaimer, the term of this patent is extended or adjusted under 35 U.S.C. 154(b) by 1272 days.

(21) Appl. No.: 14/838,546

(22) Filed: Aug. 28, 2015

(65) Prior Publication Data

US 2016/0070883 A1    Mar. 10, 2016

Related U.S. Application Data

(60) Provisional application No. 62/046,202, filed on Sep. 5, 2014.

(51) Int. Cl.
| | |
|---|---|
| *G06F 19/00* | (2018.01) |
| *G16H 10/60* | (2018.01) |
| *G16H 10/20* | (2018.01) |

(52) U.S. Cl.
CPC .............. *G16H 10/60* (2018.01); *G06F 19/00* (2013.01); *G16H 10/20* (2018.01)

(58) Field of Classification Search
CPC ........... A61N 1/08; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 10/10; G06Q 40/08; G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70;
(Continued)

(56) References Cited

U.S. PATENT DOCUMENTS 6,196,970 B1 *   3/2001   Brown ................. A61B 5/0002
                                                                600/300

* cited by examiner

*Primary Examiner* — Maroun P Kanaan (57) ABSTRACT

The execution of a clinical trial is supported in the following manner. Patient model data is provided for modeling a patient-level workflow in the clinical trial in accordance with a trial protocol. Clinical data of patients participating in the clinical trial is accessed. Using a workflow engine, an instance of the patient-level workflow is instantiated for each of the patients to obtain a plurality of patient-level workflow instantiations. Each of the patient-level workflow instantiations is executed independently based on the clinical data of each respective one of the patients. The patient model data may include or be linked to a rule associated with a step of the patient-level workflow. The rule may be executed when the workflow engine reaches the step in one of the patient-level workflow instantiations. Accordingly, a virtual representation of the clinical trial on a patient-level is obtained which represents the actual state of the clinical trial yet which is computer-accessible. Having such a virtual representation of the clinical trial allows the clinical trial to be easily monitored, actively managed, etc., thereby facilitating its execution.

16 Claims, 4 Drawing Sheets

(58) Field of Classification Search
CPC ........ G16H 20/90; G16H 30/00; G16H 30/20;
G16H 30/40; G16H 40/00; G16H 40/20;
G16H 40/40; G16H 40/60; G16H 40/63;
G16H 40/67; G16H 50/00; G16H 50/20;
G16H 50/30; G16H 50/50; G16H 50/70;
G16H 50/80; G16H 70/00; G16H 70/20;
G16H 70/14; G16H 70/60; G16H 80/00
See application file for complete search history.

FIG. 5  FIG. 6

SUPPORTING EXECUTION OF A CLINICAL TRIAL

FIELD OF THE INVENTION

The invention relates to a system and a method for supporting execution of a clinical trial. The invention further relates to model data for use in the system and method, to a computer readable medium comprising the model data, and to a computer readable medium comprising non-transitory data representing instructions for performing the method.

BACKGROUND OF THE INVENTION

Clinical trials are key instruments in clinical research that enable the validation of research hypotheses, turning them into evidence that can be applied in standard clinical care. The population to be enrolled in a trial is typically described by a set of free-text eligibility criteria. The patients selected as eligible who agree to participate in a trial will be managed according to a detailed and rigorous trial protocol. This trial protocol is typically an extensive document describing, e.g., treatment steps with their timing, potential risks, adverse effects and their management, examinations and tests, and data collection.

Execution of a clinical trial involves obtaining and evaluating clinical data.

It is known to manage the collection of such clinical data during a clinical trial using Clinical Report Forms (CRFs) that specify the clinical data to be obtained throughout the trial and will be filled in for each patient by the treating clinical site with the measured values, such as demographics, diagnosis, lab values, scans, etc. At the clinical site that leads the trial, i.e., where the principal investigator is located, the CRFs are received from all participating clinical sites. As the trial progresses, the clinical data is stored in a Clinical Trial (CT) management system. The CT management system stores the collected clinical data in a structured form. The most advanced CT management systems also provide Electronic Data Capture, by providing electronic forms through which the CRFs are filled in.

SUMMARY OF THE INVENTION

Disadvantageously, despite the use of CT management systems, the execution of a clinical trial remains a complex and expensive process that heavily relies on extensive manual coordination among clinical sites and free text documents. Typically, a trial manager will still need to ensure that the clinical sites provide the necessary clinical data for all enrolled patient in a timely fashion, ensure that all CRFs are correctly filled in, etc.

It would be advantageous to provide a system or method which supports the execution of a clinical trial by addressing one or more of the above concerns.

The following aspects of the invention involve modeling a patient-level workflow in the clinical trial in accordance with a trial protocol of the clinical trial. Using the modeling of the patient-level workflow, an instantiation of the patient-level workflow is created and executed for each of the patients participating in the clinical trial. Accordingly, the clinical trial is represented by a plurality of patient-level workflow instantiations.

A first aspect of the invention provides a system for supporting execution of a clinical trial, the clinical trial being defined by a trial protocol, the system comprising:

a model repository comprising patient model data for modeling a patient-level workflow in the clinical trial in accordance with the trial protocol, the patient model data modelling the patient-level workflow as a plurality of steps;

a clinical data interface for accessing clinical data of patients participating in the clinical trial;

a workflow engine configured for:

i) instantiating an instance of the patient-level workflow for each of the patients to obtain a plurality of patient-level workflow instantiations, and ii) executing each of the patient-level workflow instantiations independently by progressing through the plurality of steps of each of the patient-level workflow instantiations based on the clinical data of each respective one of the patients;

wherein the patient model data comprises or is linked to a rule, the e associated with a step of the patient-level workflow;

wherein the system further comprises:

a rule engine for evaluating the rule when the workflow engine reaches the step in one of the patient-level workflow instantiations to enable the workflow engine to progress through the step based on an outcome of said evaluating.

In a further aspect of the invention, patient model data is provided for modeling a patient-level workflow in a clinical trial in accordance with a trial protocol, the patient model data modelling the patient-level workflow as a plurality of steps, the patient model data comprising or being linked to a rule, the rule being associated with a step of the patient-level workflow. The patient model data may be comprised on a computer readable medium.

In a further aspect of the invention, a method is provided for supporting execution of a clinical trial, the clinical trial being defined by a trial protocol, the method comprising:

providing patient model data for modeling a patient-level workflow in the clinical trial in accordance with the trial protocol, the patient model data modelling the patient-level workflow as a plurality of steps;

accessing clinical data of patients participating in the clinical trial;

using a workflow engine:

i) instantiating an instance of the patient-level workflow for each of the patients to obtain a plurality of patient-level workflow instantiations, and ii) executing each of the patient-level workflow instantiations independently by progressing through the plurality of steps of each of the patient-level workflow instantiations based on the clinical data of each respective one of the patients;

wherein the patient model data comprises or is linked to a rule, the rule being associated with a step of the patient—level workflow;

wherein the method further comprises, using a rule engine:

evaluating the rule when the workflow engine reaches the step in one of the patient-level workflow instantiations to enable the workflow engine to progress through the step based on an outcome of said evaluating.

In a further aspect of the invention, a computer readable medium is provided comprising non-transitory data representing instructions for causing a processor system to perform the method.

The above aspects involve providing patient model data which models a patient-level workflow in a clinical trial. The patient-level workflow is modelled based on the trial protocol, based on such a trial protocol describing the overall framework as well as details of the clinical trial, in terms of treatment steps, timing, potential risks, adverse effects and their management, examinations and tests, data collection, etc. Here, the adjective 'patient-level' refers to the workflow representing the clinical trial at the level of a patient, rather than, e.g., at a higher, meta-level of the clinical trial. A clinical data interface is provided for accessing clinical data of the patients participating in the trial. Such clinical data may be dynamic, in that data may become available during the course of the clinical trial.

A workflow engine is provided. Here, the term 'engine' refers to a software framework, which may be functionally coupled to execution hardware and/or execution software (e.g., a virtual machine). The workflow engine is configured for, based on the patient model data, instantiating an instance of the patient-level workflow for each of the patients. It is noted that the concept of instantiating is known per se from the field of computer science, and that throughout this text, the terms 'instance' and 'instantiation' are used interchangeably. As such, a plurality of patient-level workflow instances are obtained.

The workflow engine is further configured for executing each of the patient-level workflow instantiations independently based on the clinical data of each respective one of the patients. Accordingly, each instantiation may be represented by a separate software thread or software process. However, this is not a limitation, in that other embodiments of independent instantiations are equally conceivable within a software framework.

To support the modeling of a patient-level workflow, the patient model data comprises or is linked to a rule for being evaluated as part of the execution of a patient-level workflow instance. The rule is associated with a particular step of the patient-level workflow. A rule engine is provided for evaluating the rule when the workflow engine reaches the step in one of the patient-level workflow instantiations. For example, the rule engine may be triggered by the workflow engine upon reaching the step, and the workflow engine may use an outcome of the evaluation of the rule in further progressing through the patient-level workflow instantiation. Additionally or alternatively, the evaluation of the rule may also have a further objective in the execution of the patient-level workflow instantiation which is not directly used in progressing through the patient-level workflow instantiation.

The above measures have the effect that the clinical trial is modeled, at least on a patient-level, by patient model data. This patient model data enables the workflow engine to create instances of the patient-level workflow for each patient participating in the clinical trial. By providing a rule engine, rules associated with the patient-level workflow can be evaluated and the outcome used in the execution of workflow instances. As such, the system effectively obtains a virtual representation of the clinical trial on a patient-level which represents the actual state of the clinical trial yet which is computer-accessible. Having such a virtual representation of the clinical trial allows the clinical trial to be easily monitored, actively managed, etc. Advantageously, the execution of a clinical trial is facilitated.

Optionally, the model repository further comprises trial model data for modeling a meta-level workflow of the clinical trial in accordance with the trial protocol, the trial model data models the meta-level workflow as a plurality of steps, and the workflow engine is configured for:
i) instantiating an instance of the level workflow to obtain a meta-level workflow instantiation, and
ii) executing the meta-level workflow instantiation by progressing through the plurality of steps of the meta-level workflow instantiation based on input obtained from the plurality of patient-level workflow instantiations.

In addition to the patient model data which models the clinical trial as a workflow on a patient-level, trial model data is provided which models the clinical trial as a workflow on a meta-level. Here, the term 'meta-level' refers to the workflow representing the clinical trial above the patient-level, e.g., across several or all of the patients. As such, the meta-level workflow represents the clinical trial on a higher level. For example, the meta-level workflow may define tasks to be performed across several instances of the patient-level workflow based on input obtained from the plurality of patient-level workflow instantiations. Effectively, the 'meta-level' may be understood as a 'coordination level', referring to the modelled workflow coordinating between several instances of the patient-level workflow.

By instantiating one instance of the meta-level workflow for a clinical trial, and by executing the meta-level workflow instantiation based on input obtained from the plurality of patient-level workflow instantiations, a more complete virtual representation of the clinical trial is obtained in that it represents not only the actual state of the clinical trial on the level of the individual patients but also on a level above the patient level.

Optionally, the workflow engine is configured for using as input in the execution of the meta-level workflow instantiation one or more of state information describing a state of the patient-level workflow instantiations, and the clinical data obtained during the execution of the patient-level workflow instantiations. By executing the patient-level workflow instantiations, the state of each instantiation is known to the workflow engine. Here, the term state may refer to the progress in the particular workflow instance. For example, if the patient-level workflow is comprised of a plurality of step, the state may identify the current step. Additionally or alternatively, the state may refer to other types of information such as a possible event, a clinical outcome, etc. The meta-level workflow instantiation may thus use as input such state information. Additionally or alternatively, the clinical data obtained during the clinical trial may be used as input by the workflow engine.

Optionally, the trial model data defines a stopping criterion of the clinical trial, and the workflow engine is configured for:
evaluating the stopping criterion during the execution of the meta-level workflow instantiation; and
generating a stopping alert signal when the stopping criterion is met.

A trial protocol typically describes one or more stopping criteria of a clinical trial. By the trial model data defining at least one of these stopping criteria, the workflow engine is enabled to evaluate the stopping criterion during the execution of the meta-level workflow instantiation, and generating a stopping alert signal when the stopping criterion is met. It is noted that the stopping criterion is an example of a coordination action that involves each of the patient-level workflow instantiations. Alternatively, the trial model data may define any other type of coordination action for evaluation by the workflow engine.

Optionally, the workflow engine is configured for:
identifying a pattern in the execution of the patient-level workflow instantiations, the pattern representing a deviation from the trial protocol;
generating a pattern alert signal identifying the pattern.

The pattern may be a pattern across several or all of the patients. The workflow engine may identify such a pattern by having access to the plurality of patient-level workflow instantiations, and thus information such as state information, possible events, clinical outcomes, etc., as well as the clinical data used in the execution of the patient-level workflow instantiations. By identifying the pattern and generating a corresponding alert signal, a user such as a trial manager may learn of, and possibly act upon the pattern.

Optionally, the clinical data interface comprises a user interface subsystem configured for prompting a user to obtain and/or input at least part of the clinical data. Accordingly, the system actively prompts a user, such as a clinical, trial manager, etc., to obtain and/or input at least part of the clinical data. Here, the term 'obtain' may refer to the user being prompted to gather the clinical data, e.g., by scheduling or performing clinical tests, evaluating recorded measurement data, etc. It is therefore not needed for the user to manually mind the timing of obtaining and/or inputting such clinical data. Rather, the system facilitates that such clinical data is obtained and/or inputted in a timely fashion.

Optionally, the patient model data is indicative of the clinical data to be obtained in a step in the patient-level workflow, and the user interface subsystem is configured for prompting the user to obtain and/or input said clinical data when the workflow engine reaches the step in one of the patient-level workflow instantiations. The user is thus prompted to obtain and/or input the clinical data at the appropriate moment in time, namely when a patient-level workflow instantiation arrives at a step where clinical data is needed.

Optionally, the patient model data comprises or is linked to a data input form for use in inputting the clinical data to be obtained in the step in the patient-level workflow, and the user interface subsystem is configured for enabling the user to input said clinical data using the data input form. The input of the clinical data may be facilitated by the system providing a data input form for use in inputting the clinical data. Such a data input form may be data-specific, e.g., by being tailored to the type of clinical data having to be input.

Optionally, the rule engine is configured for evaluating the rule of a particular patient-level workflow instantiation based on the clinical data of a respective one of the patients. A rule may use as input clinical data of a respective one of the patients. Accordingly, the rule engine is enabled to evaluate the clinical data. Advantageously, the workflow engine may progress through the respective patient-level workflow initiation based on an outcome of the evaluation of a rule having the patient's clinical data as input.

Optionally, the rules define one or more of: a threshold for use in evaluating the clinical data, a deadline associated with the execution of the step of the patient-level workflow, and error detection logic for detecting an inconsistency or error in the clinical data. By a rule defining error detection logic, the rule engine is enabled to detect errors in the clinical data. In particular, the rule engine may detect errors in newly obtained clinical data, such as clinical data having been input by a user in response to a prompt by the system. For example, missing values, wrong units, wrong data types, impossible values, etc., may be automatically detected by the rule engine. Accordingly, an alert signal may be generated notifying the user of an inconsistency or error having been detected in the clinical data.

Optionally, the plurality of steps of the patient level workflow define one or more of: a task or action to be performed by a user, a clinical condition to be met, timing information prescribing an execution timing of a respective step, a link to a rule for evaluating progression through the respective step, and a link to a data input form for use in inputting clinical data to be obtained in the respective step. Such type of patient model data allows the clinical trial to be accurately modeled on a patient-level.

In accordance with the above, the execution of a clinical trial may be supported in the following manner. Patient model data may be provided for modeling a patient-level workflow in the clinical trial in accordance with a trial protocol. Clinical data of patients participating in the clinical trial may be accessed. Using a workflow engine, an instance of the patient-level workflow may be instantiated for each of the patients to obtain a plurality of patient-level workflow instantiations. Each of the patient-level workflow instantiations may be executed independently based on the clinical data of each respective one of the patients. The patient model data may comprise or be linked to a rule associated with a step of the patient-level workflow. The rule may be executed when the workflow engine reaches the step in one of the patient-level workflow instantiations. Accordingly, a virtual representation of the clinical trial on a patient-level may be obtained which represents the actual state of the clinical trial yet which is computer-accessible. Having such a virtual representation of the clinical trial may be allows the clinical trial to be easily monitored, actively managed, etc., thereby facilitating the execution of the clinical trial.

It will be appreciated by those skilled in the art that two or more of the above-mentioned embodiments, implementations, and/or aspects of the invention may be combined in any way deemed useful.

Modifications and variations of the patient model data, the method, and/or the computer readable medium, which correspond to the described modifications and variations of the system, can be carried out by a person skilled in the art on the basis of the present description.

The invention is defined in the independent claims. Advantageous yet optional embodiments are defined in the dependent claims.

BRIEF DESCRIPTION OF THE DRAWINGS

These and other aspects of the invention are apparent from and will be elucidated with reference to the embodiments described hereinafter. In the drawings.

It should be noted that items which have the same reference numbers in different drawings, have the same structural features and the same functions, or are the same signals. Where the function and/or structure of such an item has been explained, there is no necessity for repeated explanation thereof in the detailed description.

LIST OF REFERENCE NUMBERS

The following list of reference numbers is provided for facilitating the interpretation of the drawings and shall not be construed as limiting the claims.
020 clinical data repository
022 accessing of clinical data
030 clinical data
040 display
042 display data
060 user input device
062 user input
100 system for supporting execution of a clinical
110 model repository
120 patient model data
130 trial model data
140 clinical data interface comprising user interface subsystem
142 clinical data accessed through clinical data interface
150 workflow engine
152 internal data communication
160 rule engine
170 event detector
180 notification subsystem
200 patient-level workflow in clinical trial
201-216 plurality of steps of patient-level workflow
220-224 start/end nodes
230-232 decision nodes
240-245 timing nodes
300 meta-level workflow of clinical trial
301-306 plurality of steps of meta-level workflow
320-321 start/end nodes
331-332 decision nodes
400 method for supporting execution of a clinical trial
410 providing patient model data
420 accessing clinical data
430 instantiating instances of patient-level workflow
440 executing instances of patient-level workflow
450 executing rule associated with patient-level workflow
500 computer readable medium
510 instructions stored on computer readable medium as non-transitory data
600 computer readable medium
610 model data stored on computer readable medium as non-transitory data

DETAILED DESCRIPTION OF EMBODIMENTS

Figure 1:
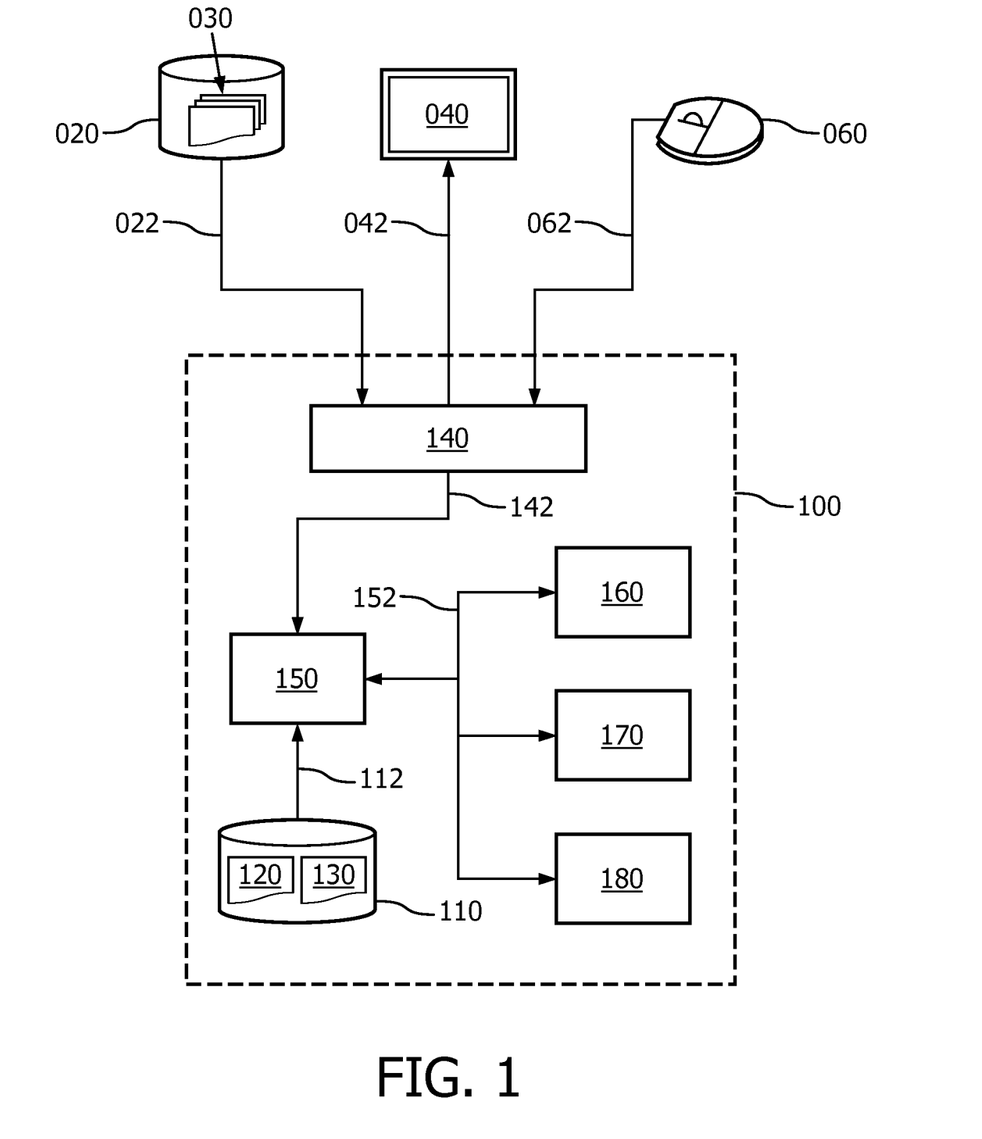
FIG. 1 shows a system for supporting execution of a clinical trial, the system comprising a workflow engine, a rule engine and being shown to comprise optional aspects such as a user interface subsystem for interacting with a user.

FIG. 1 shows a system 100 for supporting execution of a clinical trial which is defined by a trial protocol. The system 100 comprises a model repository 110 comprising patient model data 120 for modeling a patient-level workflow in the clinical trial in accordance with the trial protocol. As will be further discussed with reference to FIG. 2, such patient model data 120 may take various forms. In particular, the patient model data 120 may be formatted in accordance with a predefined standard, e.g., a standard representation. The patient model data 120 may comprises or be linked to one or more rules. The one or more rules may be associated with one or inure step of the patient-level workflow. A linking to a rule may involve the patient model data 120 referencing to a rule repository (not shown).

The system 100 further comprises a clinical data interface 140 for accessing clinical data of patients participating in the clinical trial. In the example of FIG. 1, two different options are shown for the clinical data interface 140 accessing such clinical data. Both options may be combined or used individually. Namely, the clinical data interface 140 is shown to access 022 the clinical data 030 on an external clinical data repository 020. In accordance with this example, the clinical data interface 140 may comprise, or be constituted by, a network interface such as a local or wide area network interface connected to, e.g., a Hospital Information System (HIS) or the Internet. The clinical data repository 020 may be part of a clinical trial management system for centrally storing clinical data of patients participating in the clinical trial in a structured form. The system 100 may be connected or comprised in the clinical trial management system. Another example is that the clinical data 030 may be provided by, or comprised in, an Electronic Health Record (EHR). Accordingly, the clinical data repository 020 may be constituted by an EHR database. It is noted that, in addition to clinical data, also other types of data of the patients may be accessed, such as administrative data as obtained from, e.g., an administrative data repository.

Another option shown in FIG. 1 involves the clinical data interface 140 comprising, or being constituted by, a user interface subsystem configured for prompting a user to obtain and/or input at least part of the clinical data. For that purpose, the clinical data interface 140 may provide display data 042 to a display 040 and receive user input 062 from a user via a user input device 060, such as a computer mouse 060, keyboard, touchscreen, etc.

The system 100 further comprises a workflow engine 150 and a rule engine 160. The workflow engine 150 and the rule engine 160 are shown to communicate with each other using internal data communication 152. During operation of the system 100, the workflow engine 150 may, based on the patient-model data, instantiate an instance of the patient-level workflow for each of the patients to obtain a plurality of patient-level workflow instantiations. The workflow engine may further execute each of the patient-level workflow instantiations independently by progressing through the plurality of steps of each of the patient-level workflow instantiations based on the clinical data of each respective one of the patients. The clinical data may be accessed 142 by the workflow engine 150 through the clinical data interface 140. Additionally, during the operation of the system 100, the rule engine 160 may evaluate one or more rules when the workflow engine reaches a step in one of the patient-level workflow instantiations which is associated with such a rule to enable the workflow engine to progress through the step based on an outcome of said evaluating. For example, such a rule may define a threshold for use in evaluating the clinical data, a deadline associated with the execution of the step of the patient-level workflow, and error detection logic for detecting an inconsistency or error in the clinical data. Accordingly, the functionality defined by the rule may be evaluated and its result used by the workflow engine to progress through the respective patient-level workflow instantiation.

FIG. 1 further shows various optional aspect of the system 100. As explained further with reference to FIG. 3, the model repository 110 is shown to comprise trial model data 130 for modeling a meta-level workflow of the clinical trial in accordance with the trial protocol of the clinical trial, FIG. 1 further shows the system 100 comprising an event detector 170 and a notification subsystem 180. Their function will be explained onwards.

Moreover, although not explicitly shown in FIG. 1, the model repository 110 may function as a central repository storing patient model data for different types of clinical trials. Accordingly, the model repository 110 may comprise different sets of patient model data which each model a patient-level workflow in a different clinical trial.

The system 100 may be embodied as, or in, a single device or apparatus, such as a workstation or imaging apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model.

Figure 2:
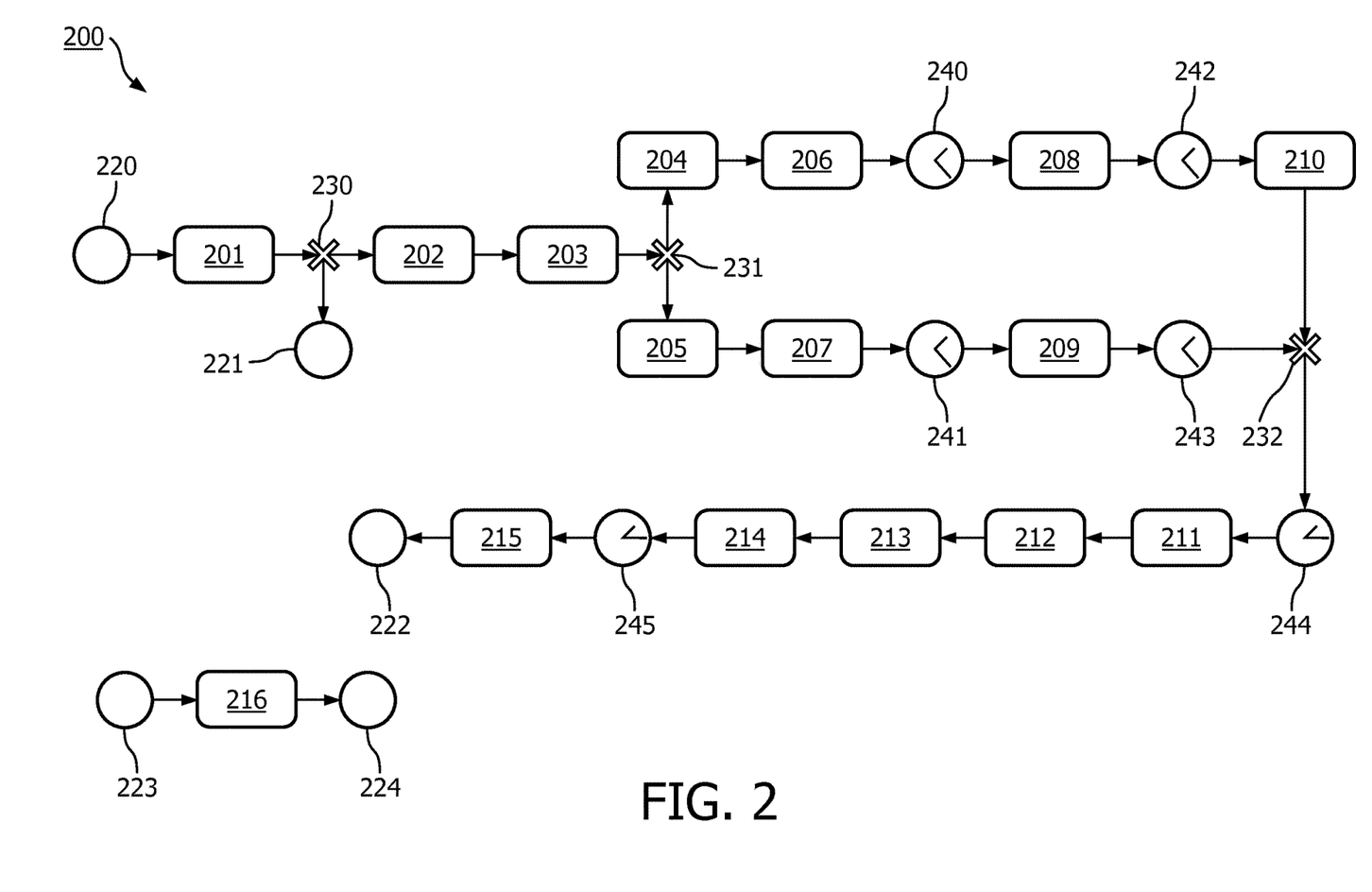
FIG. 2 shows a patient-level workflow in a clinical trial which may be instantiated by the workflow engine for several or all patient participating in the clinical trial.

FIG. 2 shows a patient-level workflow in a clinical trial which may be instantiated by the workflow engine for each patient participating in a clinical trial, or for at least for a subset of the patients participating in the clinical trial. Accordingly, for each of the patients, an instance of the patient-level workflow may be created and executed by the workflow engine based at least in part on clinical data of the respective patient.

The example of FIG. 2 involves a particular type of clinical trial. Here, the steps of the patient-level workflow 200 may be titled as follows:
201 Eligibility check
202 Chest x-ray, bone scan, biopsy
203 Randomization
204 Registration arm 2
205 Registration arm 2
206 Epirubicin cycle 1
207 Epirubicin cycle 1
208 Epirubicin cycle 2
209 Epirubicin cycle 2
210 Epirubicin cycle 3
211 Mammography, hematochemistry, ultrasound
212 Surgery
213 Taxotere 4×
214 Evaluation
215 Follow-up
216 Report SAE In general, the steps may define parts of the patient-level workflow such as, e.g., a task or action to be performed by a user, a clinical condition to be met, timing information prescribing an execution timing of a respective step, a link to a rule for evaluating progression through the respective step, and a link to a data input form for use in inputting clinical data to be obtained in the respective step. The patient-level workflow 200 is further shown to comprise start/end nodes 220-224, decision nodes 230-232 and timing nodes 240-245. Such nodes 220-245 may be defined by the patient model data.

Although not explicitly shown in FIG. 2, the respective steps may, but do not need to be, associated with rules defining, e.g., a threshold for use in evaluating the clinical data, a deadline associated with the execution of the step of the patient-level workflow, and error detection logic for detecting an inconsistency or error in the clinical data. The rules may be executed by the rule engine where required. For example, the workflow engine may trigger the rule engine, or alternatively any other external execution engine or execution logic, to execute a rule when a patient-level workflow instantiation has reached a specific step which is associated with the rule. Accordingly, advanced functionality such as error and conflict detection may be supported by the patient-level workflow. Also, using such rules, additional engines or external services may be invoked for more advanced functionality, e.g., in case such functionality cannot by handled by the rule engine. For example, an external analysis algorithm may be implemented as a service or a program and be started or executed by the patient-level workflow instantiation via the rule engine.

The patient model data may be indicative of the clinical data to be obtained in a step in the patient-level workflow. For example, a step may indicate that a hematochemistry needs to be performed and the results inputted into the system. The user interface subsystem may be configured for prompting the user to obtain and/or input said clinical data when the workflow engine reaches the step in one of the patient-level workflow instantiations. To facilitate such input, the patient model data may comprise or be linked to a data input form for use in inputting the clinical data. The data input form may be established via the user interface subsystem. For example, the data input form may be a web-based form which enables the user to input the clinical data by filling out input fields of the web-based form.

Figure 3:
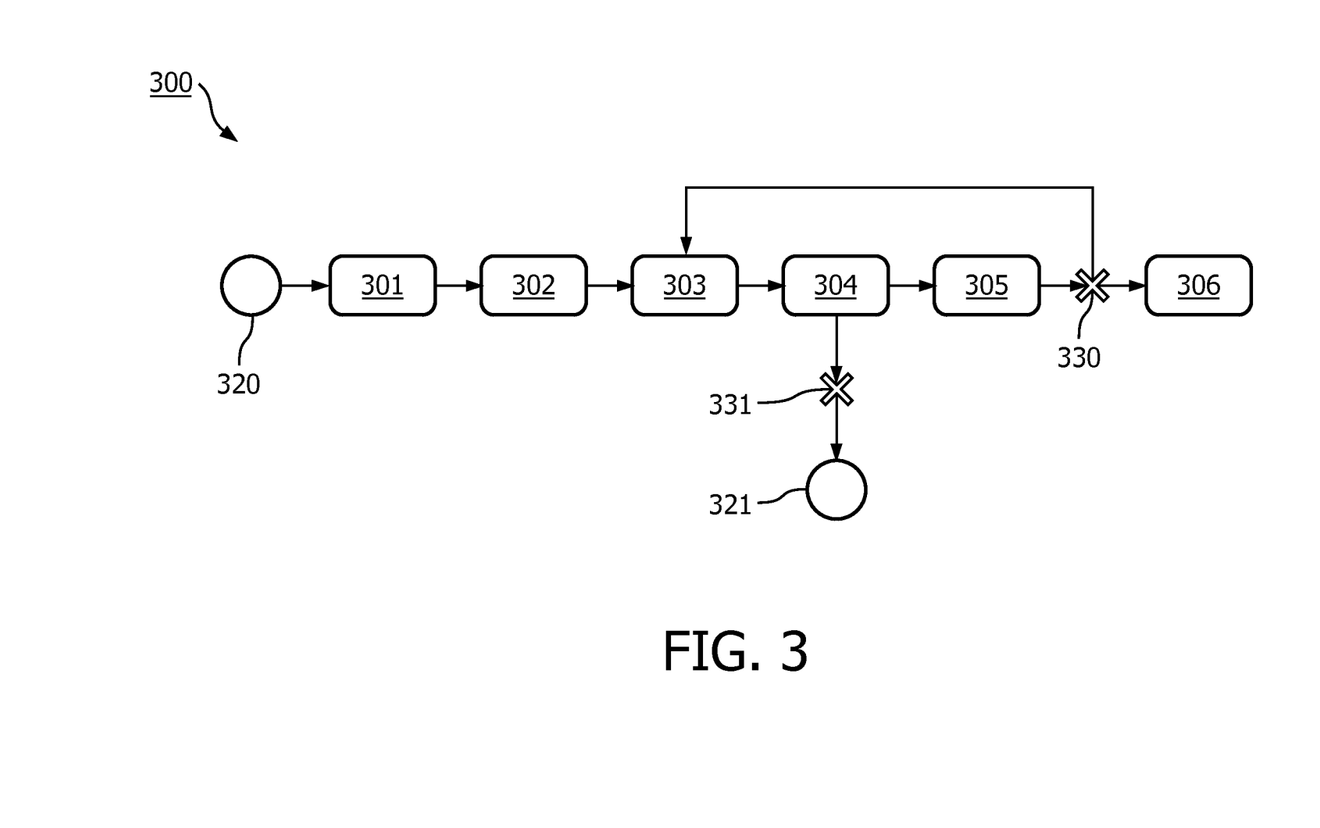
FIG. 3 shows a meta-level workflow of the clinical trial which may be instantiated once by the workflow engine for the clinical trial.

The model repository may further comprise trial model data for modeling a meta-level workflow of the clinical trial in accordance with the trial protocol. FIG. 3 shows an example of such a meta-level workflow 300 for the clinical trial of which FIG. 2 shows a patient-level workflow. The workflow engine may be configured for instantiating an instance of the meta-level workflow 300 to obtain a meta-level workflow instantiation, and executing the meta-level workflow instantiation based on input obtained from the plurality of patient-level workflow instantiations. In the example shown in FIG. 3, the steps of the meta-level workflow 300 may be titled as follows:
301 Select cohort
302 Start enrollment
303 Oversee running instances
304 Monitor SAE's
305 Data analytics
306 Final reporting The meta-level workflow 300 is further shown to comprise start/end nodes 320-321 and decision nodes 330-331. Such nodes 320-331 may be defined by the trial model data. Additionally or alternatively, the trial model data may define a stopping criterion of the clinical trial. For example, in the example of the meta-level workflow 300 of FIG. 3, the decision node 331 may be labeled "Stop trial in case of nr. of SAE>5%". Here, the abbreviation 'SAE' refers to 'Serious Adverse Event'. The workflow engine may be configured for evaluating the stopping criterion during the execution of the meta-level workflow instantiation. For example, the workflow engine 150 may determine from the plurality of patient-level workflow instantiations how many Serious Adverse Events have occurred. The workflow engine 150 may be further configured for generating a stopping alert signal when the stopping criterion is met. Such a stopping alert signal may be notified to a user, e.g., using the notification subsystem 180 shown in FIG. 1. For example, the notification subsystem 180 may send an electronic message to a user alerting the user of the stopping criterion having been met. Additionally or alternatively, an onscreen message may be displayed on a display 40.

For detecting such SAE's and/or other types of events, the system may comprise an event detector, as shown earlier in FIG. 1. The event detector 170 may provide input to patient-level workflow instantiations and/or the meta-level workflow instantiation about relevant events, such as exceptions, errors, relevant time points or thresholds reached by instances, etc., which may influence the clinical trial either at the patient-level or at the meta-level. For that purpose, the event detector 170 may monitor the data stored for each workflow instantiation and the execution of said instantiation. Accordingly, when a relevant event is detected, the event detector may trigger the workflow engine 150 so as to enable the workflow engine to progress to an appropriate part in the respective workflow. Accordingly, the workflow engine may executing the patient-level workflow instantiations and/or the meta-level workflow instantiation further based on input obtained from the event detector.

Additionally or alternatively to the workflow engine 150 being configured for determining when a stopping criterion is met, the workflow engine may be configured for identifying a pattern in the execution of the patient-level workflow instantiations, and for generating a pattern alert signal identifying the pattern. Such a pattern alert signal may be notified to a user, e.g., using the notification subsystem shown in FIG. 1. For example, the notification subsystem 180 may send an electronic message to a user alerting the user of the pattern having been identified in the execution of the patient-level workflow instantiations. Additionally or alternatively, the identification of the pattern and/or the generation of the pattern alert signal may be recorded, e.g., in a log-file. The pattern may represent a deviation from the trial protocol. In order to determine this deviation, a norm may be made known to the workflow engine 150. For example, the patient model data and/or the trial model data may identify this norm, thereby enabling the workflow engine to determine the deviation from the norm in the execution of the patient-level workflow instantiations FIG. 1, 2.

It will be appreciated that the above measures may be advantageously used to provide a clinical trial management system that improves efficiency and accuracy of clinical trial execution, namely by modelling and managing clinical trials as workflow-supported active entities (workflow-driven software agents). These active entities may 'pull' the necessary information from the participating clinical sites at the right moment according to the trial protocol, store and manage the clinical data and run automatic checks to detect potential errors and inconsistencies in the clinical data (e.g. missing values wrong units, wrong data types, impossible values, etc.). For each detected inconsistency an exception may be raised and a user may be notified. A two-level representation of each clinical trial may be provided. The first level may provide a workflow representation for describing the path of a patient through the clinical trial, which will be instantiated for each patient and executed. Additionally, each clinical trial may be described by a meta-workflow having a single instance for each clinical trial. The meta-level workflow may manage advanced functionality across patient-level instances of the clinical trial. Examples of such tasks of the meta-level workflow may include the monitoring of the recruitment of patients, the carrying out of preliminary analyses and the analysis at the end of the clinical trial, the identifying stopping criteria, identifying patterns in the individual workflows, issues with data capture, etc. In other words, the meta-level workflow may govern the overall execution of the clinical trial and may coordinate, when needed, across patient-level instances, by monitoring exceptions, errors, stopping conditions. In a specific example of a Severe Adverse Event (SAE) whose frequency is above a given threshold, the meta-level workflow instantiation may inform an end-user that the stopping criterion has been reached. Additionally or alternatively, a rule may be activated which stops all patient-level workflow instances.

In order to deploy the above described clinical trial management system, the model repository may be populated with models and descriptions of the clinical trials that are relevant for the clinical organization that will access the system. For that purpose, a domain knowledge expert and an administrator/IT expert may be involved to generate the model data modelling the patient-level workflow and/or the meta-level workflow in accordance with the trial protocol, to define the participating sites, and to implement sets of rules. The model repository may be updated when new clinical trials are set up, current clinical trials receive amendments or new clinical sites join a clinical trial. The clinical trial management system may be deployed at a data center or at the site of the principal investigator. The workflow engine and the rule engine may be central components of the clinical trial management system and may be run at a designated site for a group of hospitals that collaborate in one or multiple clinical trials. However, this is not a limitation, in that said engines may also run locally at a site when required, outside the hospital in an external data center, etc.

It is noted that, although not described with reference to FIGS. 1-3, the system may further comprise, or be connectable to, a visualization module and workflow editor enabling users to browse and update the repository of clinical trials by adding new clinical trials, by updating models of a clinical trial when trial amendments are created, to associate new error detection rules, to update data input forms, etc. The system may also enable users to, via a user interface, start clinical trials, view clinical trials, input clinical data, explore the results of the meta-level workflow tasks such as meta-analysis, alerts, etc.

Figure 4:
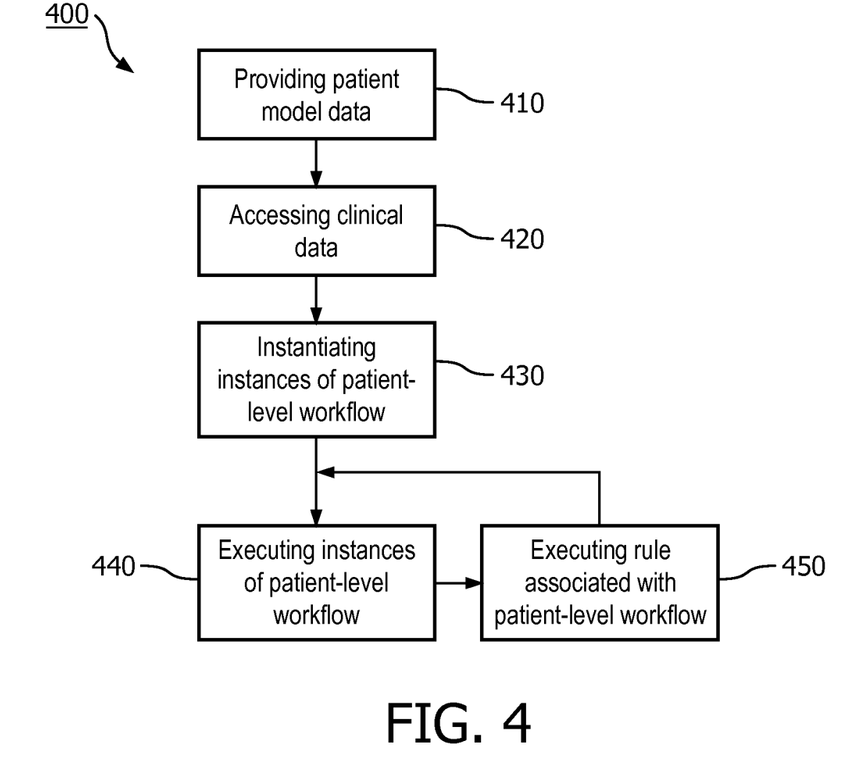
FIG. 4 shows a method for supporting execution of a clinical trial.

FIG. 4 shows a method 100 for supporting execution of a clinical trial. The method 400 may correspond to an operation of the system 100 of FIG. 1. However, this is not a limitation, in that the method 400 may also be performed in separation of the system 100 of FIG. 1, e.g., using one or more different devices or apparatuses.

The method 400 comprises, in an operation titled "PROVIDING PATIENT MODEL DATA", providing 410 patient model data for modeling a patient-level workflow in the clinical trial in accordance with the trial protocol, the patient model data modelling the patient-level workflow as a plurality of steps. The method 400 further comprises, in an operation titled "ACCESSING CLINICAL DATA", accessing 420 clinical data of patients participating in the clinical trial. The method 400 further comprises, in an operation titled "INSTANTIATING INSTANCES OF PATIENT-LEVEL WORKFLOW", using a workflow engine to instantiate 130 an instance of the patient-level workflow for each of the patients to obtain a plurality of patient-level workflow instantiations. The method 400 further comprises, in an operation titled "EXECUTING INSTANCES OF PATIENT-LEVEL WORKFLOW", executing 440 each of the patient-level workflow instantiations independently by progressing through the plurality of steps of each of the patient-level workflow instantiations based on the clinical data of each respective one of the patients. The method 400 further comprise, in an operation titled "EVALUATING RULE(S) ASSOCIATED WITH PATIENT-LEVEL WORKFLOW", using a rule engine to evaluate 450 the rule when the workflow engine reaches the step in one of the patient-level workflow instantiations to enable the workflow engine to progress through the step based on an outcome of said evaluating.

It will be appreciated that the above operation may be performed in any suitable order, e.g., consecutively, simultaneously, iteratively or a combination thereof, subject to, where applicable, a particular order being necessitated, e.g., by input/output relations. For example, the operations of accessing the clinical data of patients, executing the patient-level workflow instantiations and executing rule(s) associated with steps in the patient-level workflow instantiations may be performed iteratively in that clinical data may be accessed when it becomes available or is needed in one of the patient-level workflow instantiations and rule(s) are executed when needed in a patient-level workflow instantiation.

Figure 5:
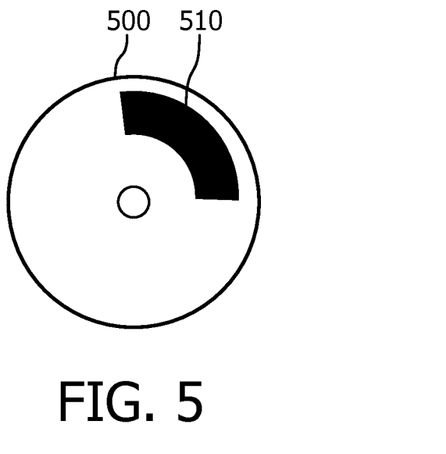
FIG. 5 shows a computer readable medium comprising non-transitory data representing instructions for causing a processor system to perform the method.

The method 400 may be implemented on a computer as a computer implemented method, as dedicated hardware, or as a combination of both. As also illustrated in FIG. 5, instructions for the computer, e.g., executable code, may be stored on a computer readable medium 500, e.g., in the form of a series 510 of machine readable physical marks and/or as a series of elements having different electrical, e.g., magnetic, or optical properties or values. The executable code may be stored in a transitory or non-transitory manner. Examples of computer readable mediums include memory devices, optical storage devices 500, integrated circuits, servers, online software, etc. FIG. 5 shows an optical disc.

Figure 6:
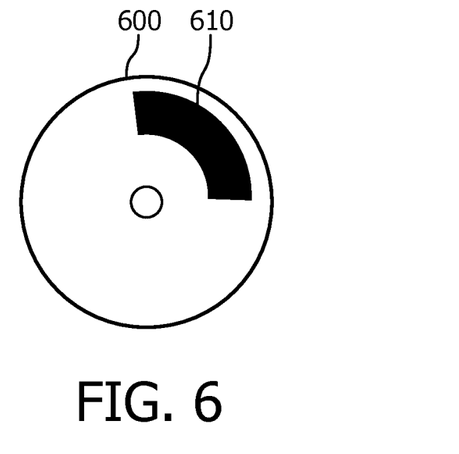
FIG. 6 shows a computer readable medium comprising patient model data in non-transitory form for modeling the patient-level workflow in a clinical trial.

FIG. 6 shows a computer readable medium 600 comprising the patient model data. The patient model data may be may be stored on the computer readable medium 600, e.g., in the form of a series 610 of machine readable physical marks and/or as a series of elements having different electrical, e.g., magnetic, or optical properties or values. The patient model data may be stored in a transitory or non-transitory manner. Although not explicitly shown in FIG. 6, the computer readable medium 600 may also comprise the trial model data, additionally or alternatively to comprising the patient model data.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g., at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for supporting execution of a clinical trial, the clinical trial being defined by a trial protocol including treatment steps, timing, potential risks, adverse effects and their management, examinations, tests, and data collection for the clinical trial, the system comprising:
   a memory configured to store:
      patient model data for modeling a patient-level workflow for each patient in the clinical trial based on the treatment steps, the timing, the potential risks, the adverse effects and their management, the examinations, the tests, and the data collection, the patient-level workflow being modeled as a first plurality of steps, each step being linked to a rule, and;
      trial model data for modeling a meta-level workflow of the clinical trial across all patients based on the trial protocol, the trial model data modeling the meta-level workflow as a second plurality of steps;
   a clinical data interface configured to access clinical data of patients participating in the clinical trial during a course of the trial, the stored patient model data including rules associated with the plurality of first steps of the patient-level workflow;
   a computer processor configured to:
      i) execute the patient-level workflow for each patient independently by progressing through the first plurality of steps based on the accessed clinical data of each respective one of the patients;

ii) execute the meta-level workflow by progressing through the second plurality of steps, iii) evaluate the rule linked to each step of the first plurality of steps as the computer processor reaches each of the first plurality of steps of the patient-level workflow of each of the patients to progress through each of the first plurality of steps, iv) identify a pattern in the execution of the first plurality of steps of the patient-level workflow across the patients, the pattern representing a deviation from the trial protocol and generate a pattern alert signal identifying the pattern, and v) evaluate a stopping criterion for the clinical trial during the execution of the second plurality of steps of the meta-level workflow, and generate a stopping alert signal when the stopping criterion is met; and a notification system configured to send at least one of the stopping alert signal and the pattern alert signal to a user of the clinical support system.

2. The system according to claim 1, further including:
a display configured to display messages indicative of at least one of the stopping criteria being met and the identification of the pattern.

3. The system according to claim 2, wherein the display is further configured to display prompts prompting the user to obtain or input data.

4. A system for supporting execution of a clinical trial, the clinical trial being defined by a trial protocol, the system comprising:
a model repository comprising:
patient model data configured to model a patient-level workflow in the clinical trial in accordance with the trial protocol, wherein the patient model data comprises or is linked to a rule, the rule being associated with a step of the patient-level workflow, the patient model data modeling the patient-level workflow as a plurality of steps, and
trial model data for modeling a meta-level workflow of the clinical trial in accordance with the trial protocol, the trial model data modeling the meta-level workflow as a plurality of steps, wherein the trial model data defines a stopping criterion of the clinical trial;
a clinical data interface configured to access clinical data of patients participating in the clinical trial;
a workflow engine configured to:
i) instantiate an instance of the patient-level workflow for each of the patients to obtain a plurality of patient-level workflow instantiations,
ii) execute each of the patient-level workflow instantiations independently by progressing through the plurality of steps of each of the patient-level workflow instantiations based on the clinical data of each respective one of the patients;
iii) instantiate an instance of the meta-level workflow to obtain a meta-level workflow instantiation,
(iv) execute the meta-level workflow instantiation by progressing through the plurality of steps of the meta-level workflow instantiation based on input obtained from the plurality of patient-level workflow instantiations, the input including one or more of: state information describing a state of the patient-level workflow instantiations, and the clinical data obtained during the execution of the patient-level workflow instantiations;

(v) evaluate the stopping criterion during the execution of the meta-level workflow instantiation, (vi) generate a stopping alert signal when the stopping criterion is met, (vii) identify a pattern in the execution of the patient-level workflow instantiations, the pattern representing a deviation from the trial protocol, (viii) generate a pattern alert signal identifying the pattern, and (ix) send at least one of the stopping alert signal and the pattern alert signal to an interface to alert a user.

5. The system according to claim 4, wherein the clinical data interface comprises a user interface subsystem configured for prompting a user to obtain and/or input at least part of the clinical data.

6. The system according to claim 5, wherein the patient model data is indicative of the clinical data to be obtained in each step in the patient-level workflow, and wherein the user interface subsystem is configured for prompting the user to obtain and/or input said clinical data when the workflow engine reaches the step in one of the patient-level workflow instantiations.

7. The system according to claim 6, wherein the patient model data comprises or is linked to a data input form for use in inputting the clinical data to be obtained in the step in the patient-level workflow, and wherein the user interface subsystem is configured for enabling the user to input said clinical data using the data input form.

8. The system according to claim 4, wherein the rule engine is configured for evaluating the rule of a particular patient-level workflow instantiation based on the clinical data of a respective one of the patients.

9. The system according to claim 8, wherein the rules define one or more of: a threshold for use in evaluating the clinical data, a deadline associated with the execution of the step of the patient-level workflow, and error detection logic for detecting an inconsistency or error in the clinical data.

10. The system according to claim 8, wherein the plurality of steps of the patient level workflow define one or more of: a task or action to be performed by a user, a clinical condition to be met, timing information prescribing an execution timing of a respective step, a link to a rule for evaluating progression through the respective step, and a link to a data input form for use in inputting clinical data to be obtained in the respective step.

11. A method for supporting execution of a clinical trial, the clinical trial being defined by a trial protocol, the method comprising:
in a memory, storing:
patient model data for modeling a patient-level workflow for each patient in the clinical trial based on treatment steps, timing, potential risks, adverse effects and their management, examinations, tests, and data selection, the patient-level workflow being modeled as a first plurality of steps, each step linked to a rule, and
trial model data for modeling a meta-level workflow of the clinical trial across all patients based on the trial protocol, wherein the trial model data models the meta-level workflow as a second plurality of steps;
during a course of a trial, with a clinical data interface, accessing clinical data of patients participating in the clinical trial, the stored patient model data and rules associated with the plurality of first steps of the patient-level workflow;

with a computer processor:
- executing the patient-level workflow for each patient independently by progressing through the first plurality of steps based on the accessed clinical data of each respective one of the patients;
- executing the meta-level workflow by processing through the second plurality of steps of the meta-level workflow;
- evaluating each rule as the computer processor progresses through each of the first plurality of steps of the patient-level workflow of each of the patients,
- evaluating a stopping criterion for the clinical trial during the execution of the second plurality of steps of the meta-level workflow and generating a stopping alert signal when the stopping criteria is met; and
- sending the stopping alert signal to a user.

12. The method according to claim 11, further including:
with the processor:
- identifying a pattern in the execution of the first plurality of steps of the patient-level workflow across the patients, the pattern representing a deviation from the trial protocol and generating a pattern alert signal identifying the pattern.

13. The method according to claim 12, further including:
displaying on a display device an indication of at least one of the stopping alert signal and the pattern alert signal.

14. A non-transitory computer-readable medium for controlling a processor system to perform a method for supporting execution of a clinical trial, the clinical trial being defined by a trial protocol, the method comprising:
in a memory, storing:
- patient model data for modeling a patient-level workflow for each patient in the clinical trial based on treatment steps, timing, potential risks, adverse effects and their management, examinations, tests, and data selection, the patient-level workflow being modeled as a first plurality of steps, the steps being associated with rules;
- trial model data for modeling a meta-level workflow of the clinical trial across all patients based on the trial protocol, wherein the trial model data models the meta-level workflow as a second plurality of steps; and
- during a course of a trial with a clinical data interface, accessing clinical data of patients participating in the clinical trial, the stored patient model data and the rules associated with the plurality of first steps of the patient-level workflow;

with a computer processor:
- executing the patient-level workflow for each patient independently by progressing through the first plurality of steps based on the accessed clinical data of each respective one of the patients;
- executing the meta-level workflow by processing through the second plurality of steps of the meta-level workflow;
- evaluating each rule as the computer processor progresses through each of the first plurality of steps of the patient-level workflow of each of the patients,
- identifying a pattern in the execution of the first plurality of steps of the patient-level workflow across the patients, the pattern representing a deviation of a trial protocol,
- generating a pattern alert signal identifying the identified pattern, and
- sending the pattern alert signal to a user.

15. The non-transitory computer-readable medium according to claim 14, wherein the method further includes:
evaluating a stopping criterion for the clinical trial during the execution of the second plurality of steps of the meta-level workflow and generating a stopping alert signal when the stopping criterion is met.

16. The non-transitory computer-readable medium according to claim 15, wherein the method further includes:
controlling a display device to display an indication of at least one of the stopping criterion being met and the identified pattern.

* * * * *